United States Patent [19]

Hoehn et al.

[11] Patent Number: 4,495,179
[45] Date of Patent: Jan. 22, 1985

[54] A51568 ANTIBIOTIC AND PROCESS FOR PRODUCING THEREOF

[75] Inventors: Marvin M. Hoehn; Gary G. Marconi, both of Indianapolis, Ind.

[73] Assignee: Eli Lilly and Company, Indianapolis, Ind.

[21] Appl. No.: 562,255

[22] Filed: Dec. 16, 1983

Related U.S. Application Data

[62] Division of Ser. No. 450,880, Dec. 20, 1982, abandoned.

[51] Int. Cl.$^3$ .............. A61K 37/00; A61K 35/00; C07C 103/52
[52] U.S. Cl. .............. 514/9; 260/112.5 K; 424/118
[58] Field of Search ........... 260/112.5 R; 424/118, 424/177

[56] References Cited

U.S. PATENT DOCUMENTS

| | | | |
|---|---|---|---|
| 3,067,099 | 12/1962 | McCormick et al. | 167/65 |
| 3,338,786 | 8/1967 | Kunstmann et al. | 167/65 |
| 3,952,095 | 4/1976 | Hamill et al. | 424/118 |
| 4,322,343 | 3/1982 | Debono | 260/112.5 R |

FOREIGN PATENT DOCUMENTS 765886  1/1957  United Kingdom .

OTHER PUBLICATIONS

Williamson et al., "Structure Revision of the Antibiotic Vancomycin. The Use of Nuclear Overhauser Effect Difference Spectroscopy", J. Am. Chem. Soc. 103, 6580–6585 (1981).

Kalman et al., "An NMR Study of the Antibiotic Ristocetin A. The Negative Nuclear Overhauser Effect in Structure Elucidation" J. Am. Chem. Soc. 102, 897–905 (1980).

Ellestad et al., "Avoparcin and Epiavoparcin", J. Am. Chem. Soc. 103, 6522–6524 (1981).

Primary Examiner—Delbert R. Phillips
Attorney, Agent, or Firm—Paul C. Steinhardt; Arthur R. Whale

[57] ABSTRACT

Antibiotic A51568 is produced by submerged, aerobic fermentation of new *Nocardia orientalis* NRRL 15232. The antibiotic is gram-positive.

3 Claims, 1 Drawing Figure

A51568 ANTIBIOTIC AND PROCESS FOR PRODUCING THEREOF

This application is a division of application Ser. No. 450,880, filed Dec. 30, 1982, now abandoned.

BACKGROUND OF THE INVENTION

A great many microorganisms are pathogenic and are causative agents of disease states in both humans and animals.

Over the years, a great number of antibiotics which are active against pathogenic microorganisms have been developed. However, there is still a need to find agents which are more effective against these pathogenic microorganisms in order to more successfully treat the diseases caused by the microorganisms in humans or animals.

Antibiotic A51568, belonging to the glycopeptide family of antibiotics, is a gram-positive antimicrobial agent.

Glycopeptide antibiotics already known in the art include, inter alia, vanomycin, McCormick et al., U.S. Pat. No. 3,067,099 (Dec. 4, 1962), the structure of vancomycin being reported by Williamson et al., *J. Am. Chem. Soc.* 103, 6580–6585 (1981); actaplanin (antibiotic A-4696), Hamill et al., U.S. Pat. No. 3,952,095 (Apr. 20, 1976), a portion of the structure of actaplanin being reported by Debono, U.S. Pat. No. 4,322,343, (Mar. 30, 1982); ristocetin, British Pat. No. 765,886 (1957), the structure of ristocetin A, one factor of the ristocetin complex, being reported by Kalman et al., *J. Am. Chem. Soc.* 102, 897–905 (1980); and avoparcin, Kunstmann et al., U.S. Pat. No. 3,338,786 (Aug. 29, 1967), the structure of avoparcin being described by Ellestad et al., *J. Am. Chem. Soc.* 103, 6522–6524 (1981).

SUMMARY OF THE INVENTION

This invention relates to demethylvancomycin designated herein as antibiotic A51568, which is produced by culturing a hitherto undescribed microorganism, *Nocardia orientalis* NRRL 15232, or an A51568-producing mutant or variant thereof, under submerged aerobic fermentation conditions.

This antibiotic inhibits the growth of pathogenic microorganisms, in particular, those within the gram-positive genera Staphylococcus and Streptococcus, which are resistant to penicillin.

DESCRIPTION OF THE DRAWINGS

The infrared absorption spectrum of antibiotic A51568, run in KBr pellet, is presented in the accompanying drawing, labeled FIG. 1.

DETAILED DESCRIPTION OF THE INVENTION

This invention relates to demethylvanomycin (A-51568) having the following structural formula to its preparation, and to the pharmaceutically-acceptable, non-toxic salts of the antibiotic.

Antibiotic A51568 is a white, amorphous solid. Elemental analysis of antibiotic A51568 indicates the following approximate percentage composition: 50.63 percent carbon, 5.07 percent hydrogen, 8.36 percent nitrogen, 8.19 percent chlorine, and 25.16 percent oxygen. The antibiotic has a molecular weight of about 1435, as determined by fast-atom-bombardment mass spectrometry.

The proton nuclear magnetic resonance spectrum of antibiotic A51568 was determined in dimethylsulfoxide at 60° C. and 360 MHz. The several six-membered rings of the structural formula are identified by letters of the alphabet, as indicated in the following formula:

The table of Chemical Shifts, in ppm, follows in Table 1.

TABLE 1

Chemical Shifts

| Assignment | Chem. Shift | Assignment | Chem. Shift |
|---|---|---|---|
| Ring A | | Asparagine | |
| —NH | 6.54 | —NH | 6.61 |
| -2' | 4.19 | -α | 4.32 |
| -1' | 5.14 | -β's | 2.56 & 2.14 |
| —OH | 5.86 | | |
| -2 | 7.86 | —NH$_2$ | 7.29 & 6.83 |
| -5 | 7.30 | | |
| -6 | 7.47 | | |
| Ring B | | Leucine | |
| —NH | 8.24 | —NH$_2$ | —* |
| -1' | 5.72 | -α | 3.70 |
| -2 | 5.68 | -β's | 1.65 & 1.49 |
| -6 | 5.22 | | |
| | | -γ | 1.76 |
| | | -δ's | 0.93 & 0.90 |
| Ring C | | Glucose | |
| —NH | —* | -1 | 5.33 |
| -2' | 4.78 | -2 | 3.58 |
| -1' | 5.18 | -3 | 3.49 |
| —OH | 5.74 | -4 | 3.29 |
| -2 | 7.66 | -5 | —* |
| -3 | 7.18 | -6 | 3.70 & 3.54 |
| -6 | 7.42 | | |
| Ring D | | Vancosamine | |
| —NH | 8.45 | -1 | 5.30 |
| -1' | 4.47 | -2 | 1.93 & 1.77 |
| -2 | 6.26 | | |
| -4 | 6.42 | (3-CH$_3$) | 1.37 |
| | | 4 | —* |
| | | 5 | 4.67 |
| | | (5-CH$_3$) | 1.09 |
| Ring E | | | |
| —NH | 8.54 | | |
| -1' | 4.47 | | |
| -2 | 7.17 | | |
| -5 | 6.72 | | |
| -6 | 6.79 | | |

*Not assigned

The proton nuclear magnetic resonance spectrum of antibiotic A51568 is very much like that of vancomycin. The chief difference noticeable by inspection is the absence of the N—CH$_3$ resonance for N-(methyl)leucine in the spectrum of A51568. Thus, the proton nmr spectrum of vancomycin contains a methyl singlet at 2.34 ppm., which is absent from the proton nmr spectrum of antibiotic A51568.

Based on the molecular weight, the proton nuclear magnetic resonance spectrum data, and the elemental analyses, an empirical formula of $C_{65}H_{73}Cl_2N_9O_{24}$ is assigned to antibiotic A51568.

Potentiometric titration of antibiotic A51568 in 66 percent aqueous dimethylformamide indicated pKa values of ~6.2, 8.8, 10.3, and 12.85 (initial pH=6.12).

Antibiotic A51568 has the following specific rotation: $[\alpha]_D^{25°}$ C·=—20.4° (C=10 mg/ml, water), $[\alpha]_{365}^{25°}$ C·=—33.6° (C=10 mg/ml, water).

Figure 1:
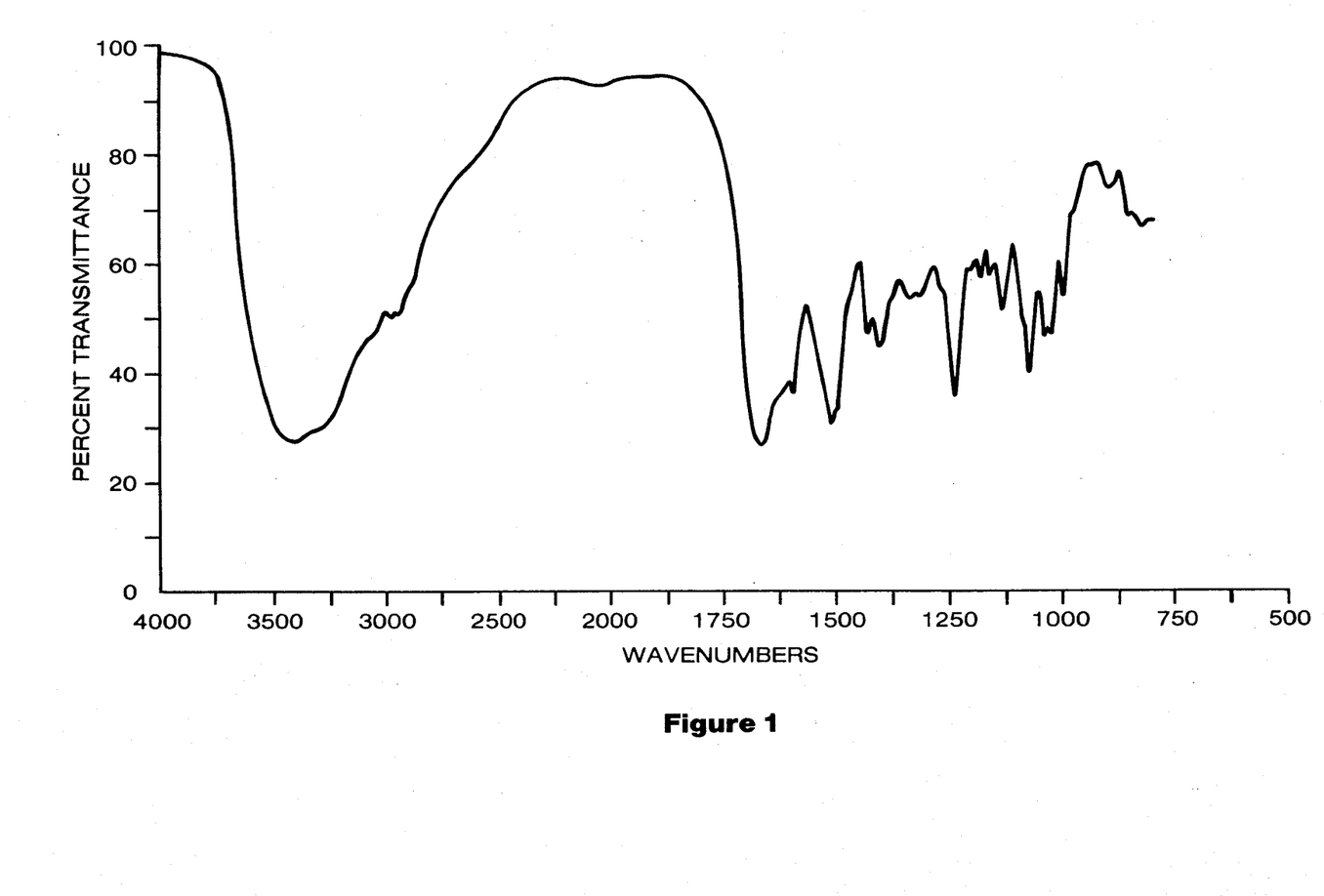

The infrared absorption spectrum of antibiotic A51568 in KBr pellet is shown in the accompanying drawing as FIG. 1. The following distinguishable absorption maxima are observed: 3400 (broad, strong), 3380 (broad, strong), 1657 (broad, strong), 1587 (medium strong), 1505 (medium strong), 1424 (medium), 1396 (medium), 1328 (broad, weak), 1310 (broad, weak), 1231 (medium strong), 1174 (weak), 1156 (weak), 1128 (medium), 1062 (medium strong), 1028 (weak), 1015 (weak), 990 (weak), 882 (weak), 881 (weak) cm$^{-1}$.

The ultraviolet absorption maxima of antibiotic A51568 in water under acid, neutral, and basic conditions are recorded in Table 2, which follows.

TABLE 2

UV Spectrophotometry of Antibiotic A51568

| Acid or Neutral max nm (ε) | Basic max nm (ε) |
|---|---|
| 278 (5,500) | 302 (6,000) |
| 234 (shoulder) (25,000) | 264 (shoulder) (10,000) |

The antibiotic substance of this invention is arbitrarily designated herein as the A51568 antibiotic.

The A51568 antibiotic substance is produced by culturing a hitherto undescribed strain of *Nocardia orientalis* NRRL 15232.

This invention further relates to the biologically pure culture of the hitherto undescribed strain of *Nocardia orientalis* NRRL 15232. For convenience, this culture has been designated in our laboratory as culture A51568.1.

Culture A51568.1 is a variant strain derived through natural selection from culture A51568, which latter culture was initially isolated from a soil sample collected in Yucatan, Mexico.

Culture A51568.1 is classified as a strain of *Nocardia orientalis* based on simultaneous laboratory comparisons, as well as comparison with the published descriptions of Nocardia by D. Berd, "Laboratory Identification of Clinically Important Aerobic Actinomycetes", *Appl. Microbiol.* 25(4), 665-681 (1973); by Bergey's Manual of Determinative Bacteriology, 8th Edition, edited by R. E. Buchanan and N. E. Gibbons (The Williams and Wilkins Co., Baltimore); by R. E. Gordon et al., "*Nocardia coeliaca, Nocardia autotrophia*, and the Nocardin Strain", *Int. J. Syst. Bacteriol.* 24(1), 54-63 (1974); by R. E. Gordon et al., "Resistance to Rifampin and Lysozyme of Strains of Some Species of Mycobacterium and Nocardia as a Taxonomic Tool", *Int. J. Syst. Bacteriol.* 27(3), 176-178 (1977); by S. A. Waksman, The Actinomycetes Vol. II, [The Williams and Wilkins Co., Baltimore (1961)]; and with the published descriptions of this species by R. E. Gordon et al., "Some Bits and Pieces of the Genus Nocardia: *N. carnea, N. vacinii, N. transvalensis, N. orientalis,* and *N. aerocolonigenes*", *J. Gen. Microbiol.* 109, 69-78 (1978); by S. J. Mishra et al., "Identification of Nocardiae and Streptomycetes of Medical Importance", *J. Clin. Microbiol.* 11(6), 728-736 (1980); and by Pittenger et al., "*Streptomyces orientalis*, n. sp., the Source of Vancomycin", Antibiot. and Chemoth. VI(11), 642-647 (1956).

The methods and media recommended for the International Streptomyces Project (ISP) for the characterization of Streptomyces species, as published by Shirling and Gottlieb ["Methods of Characterization of Streptomyces Species", *Int. J. Syst. Bacteriol.* 16(3), 313-340 (1966)], as well as methods recommended for the characterization of Nocardia species, as published by Gordon et al., "*Nocardia coeliaca, Nocardia autotrophia*, and the Nocardin Strain", *Int. J. Syst. Bacteriol.* 24(1), 54-63 (1974) were followed.

CHARACTERIZATION OF A51568.1 CULTURE

Morphology

Culture A51568.1 produces an extensive substrate and aerial mycelium. When viewed under the light microscope, the aerial hyphae have a cobweb appearance. When grown under submerged, shaken conditions, the hyphae break into short mycelial fragments.

No conidia were observed when aerial hyphae were viewed by light microscopy. However, conidia are seen when studied by scanning electron microscopy. These features are observed when culture A51568.1 is grown on ISP medium No. 5 and tap water agar. The spore surface ornamentation is smooth (Sm). The spore shape is spherical to cylindrical, and the spores are poorly and irregularly formed. This morphology is classified in the nonstreptomycetes section as described in Bergey's Manual, supra.

Cultural Characteristics

Culture A51568.1 grew well on yeast dextrose agar, as well as on many other agar media, the growth being often wrinkled and flaky. Abundant aerial mycelia were produced having a spore mass color in the gray (GY) and sometimes white (W) color series. The nearest matching color tab for the gray color series in the Tresner and Backus system [see Tresner and Backus, "System of Color Wheels for Streptomycete Taxonomy", *Appl. Microbiol.* 11, 335-338 (1956)] is d light Gray to 2dc yellowish Gray.

The aerial growth is neither as dense nor as long as typical Streptomyces. The aerial growth is produced on inorganic salts-starch agar (ISP No. 4), on glycerol-asparagine agar (ISP No. 5), and glycerol-glycine agar, and is best observed when grown on yeast-malt extract agar (ISP No. 2).

A dark brown distinctive color is observed on the reserve side in the following agar media: ISP No. 2, ISP No. 5, tyrosine agar (ISP No. 7), and glycerol-glycine agar. This color is unaffected by pH. A light to reddish brown soluble pigment is also elaborated in the above-named media, as well as in Czapek'solution agar and in glucose-asparagine agar. The reverse color of Culture A51568.1 in other media is yellow-brown.

When plated for variability, culture A51568.1 showed no mixture of colony types, and culture A51568.1 is therefore regarded as a stable isolate.

The cultural characteristics of culture A51568.1 on various media compared with the cultural characteristics of *Nocardia orientalis* ATCC 19795 are presented in Table 3, which follows.

Color names were assigned according to the ISCC-NBS Centroid Color Charts Sample No. 2106 (National Bureau of Standards, U.S. Department of Commerce, 1958), and the Color Harmony Manual, 4th Edition (Color Standards Department, Container Corporation of America, Chicago, Ill., 1958).

TABLE 3

Growth Characteristics of A51568.1 and ATCC 19795 on Various Media

| Medium | | A51568.1 | ATCC 19795 |
|---|---|---|---|
| ISP 2 | G: | Abundant-wrinkled surface | Abundant-wrinkled surface |
| | R: | 59.d.Br (no pH change) | 72.d.OY |
| | Am: | Abundant:d l. Gray (GY) | Abundant:2ba pale Yellow (Y) |
| | Sp: | Reddish-brown | None |
| ISP 3 | G: | Abundant | Abundant |
| | R: | 89.p.Y | 89.p.Y |
| | Am: | Good:d l.Gray (GY) | Good:d l.Gray (GY) |
| | Sp: | None | None |
| ISP 4 | G: | Abundant | Abundant |
| | R: | 72.d.OY | 70.1.OY |
| | Am: | Abundant:b Oyster White (W) | Abundant:b Oyster White (W) |
| | Sp: | None | None |
| ISP 5 | G: | Abundant | Abundant |
| | R: | 59.d.Br (no pH change) | 70.1.OY |
| | Am: | Abundant:b Oyster White (W) | Abundant:b Oyster White (W) |
| | Sp: | Light Brown | None |
| ISP 7 | G: | Abundant | Abundant |
| | R: | 65.br.Black (no pH change) | 71.m.OY |
| | Am: | Abundant:2ba p. Yellow (Y) | Abundant:2ba p. Yellow (Y) |
| | Sp: | Dark reddish-brown | None |
| Czapeks Solution | G: | Good | Good |
| | R: | 74.s.yBR | 70.1.OY |
| | Am: | Good:b Oyster White (W) | Good:b Oyster White (W) |
| | Sp: | Light brown | None |
| | G: | Abundant-wrinkled, flaky | Abundant-wrinkled, flaky |

TABLE 3-continued

Growth Characteristics of A51568.1 and ATCC 19795 on Various Media

| Medium | | A51568.1 | ATCC 19795 |
|---|---|---|---|
| Emerson's Agar | R: | 74.s.yBr | 74.s.yBr |
| | Am: | Good:d.1.GY→2ba p.Y (GY) | Good:2ba p. Yellow (Y) |
| | Sp: | None | None |
| | G: | Abundant | Abundant |
| Glucose Asparagine | R: | 75. deep yBr | 67. brill.OY |
| | Am: | Abundant:2dc y Gray (GY) | Abundant:2ba p. Yellow (Y) |
| | Sp: | Olive-brown | None |
| | G: | Abundant | Abundant |
| Glycerol-glycine | R: | 78.d.yB (no pH change) | 71.m.OY |
| | Am: | Abundant:2dc y Gray (GY) | Abundant:2ba p. Yellow (Y) |
| | Sp: | Olive-brown | None |
| | G: | Good | Good |
| Nutrient Agar | R: | 70.1.OY | 70.1.OY |
| | Am: | Good:b Oyster White (W) | Good:b Oyster White (W) |
| | Sp: | None | None |
| | G: | Fair | Fair |
| Tap H2O | R: | 93.y Gray | 93. y Gray |
| | Am: | Poor | Poor |
| | Sp: | None | None |
| | G: | Abundant-wrinkled, flaky | Abundant-slightly wrinkled |
| Yeast Dextrose | R: | 68.s.OY | 68.s.OY |
| | Am: | Abundant:d light Gray (GY) | Abundant:b Oyster White (W) |
| | Sp: | None | None |

G = growth
R = reverse
Am = aerial mycelia
Sp = soluble pigment

Cell Wall Studies

Using hydrolyzed whole cells of A51568.1 culture, the presence of certain diagnostic sugars was determined by the chromatographic method of M. P. Lechevalier, "Identification of Aerobic Actinomycetes of Clinical Importance", *J. Lab. Clin. Med.* 71, 931–944 (1968).

Hydrolyzed whole cells were used to determine the isomers of diaminopimelic acid according to the method of Becker et al., *Appl. Microbiol.* 11, 421–423 (1964).

The results of these studies are set forth below.

| Test | Result Observed |
|---|---|
| Diagnostic sugars | Galactose, Arabinose, Ribose |
| Isomers of 2,6-diaminopimelic acid | Meso-isomer |

These results represent a Type A whole-cell sugar pattern, and a Type IV cell wall, which combination of major cell wall constituents is indicative of the genus Nocardia. See M. P. Lechevalier, supra.

Using thin-layer chromatography of whole-cell methanolysates, according to the method described by D. E. Minnikin et al., "Differentiation of Mycobacterium, Nocardia, and Related Taxa by Thin-layer Chromatographic analysis of Whole-organism Methnolysates," *J. Gen. Microbiol.* 88, 200–204 (1975), no mycolic acid methyl esters were observed.

In addition to the above determinations, culture A51568.1 was studied and compared with published data on 21 *N. orientalis* reference strains, as well as simultaneous comparisons with NRRL 2451, NRRL 2452, and ATCC 19795. The comparison of the cultural, morphological, and physiological properties is recorded in Table 4, which follows.

TABLE 4

Comparison of Physiological Properties of A51568.1 and *N. orientalis* Reference Strains

| Characteristic | A51568.1 | NRRL 2451 | NRRL 2452 | ATCC 19795 | N. orientalis |
|---|---|---|---|---|---|
| Acid-fastness | − | − | − | − | − |
| Aerial hyphae | + | + | + | + | + |
| Catalase | + | + | + | + | + |
| Cell wall type | IV | IV | IV | IV | IV |
| Conidia | + | + | + | + | + |
| Decomposition of | | | | | |
| adenine | − | − | − | − | − |
| casein | + | + | + | + | + |
| DNA | + | + | + | + | ND |
| hypoxanthine | + | + | + | + | + |
| tyrosine | + | + | + | + | + |
| urea | + | + | + | + | + |
| xanthine | + | + | + | − | − |
| Fragmentation | + | + | + | + | + |
| Galatin liquefaction | + | + | + | + | ND |
| Gram Stain | + | + | + | + | ND |
| Hydrolysis of: | | | | | |
| esculin | + | + | + | + | + |
| hippurate | + | + | + | + | + |
| skim milk | + | + | + | + | + |
| starch | + | + | + | + | + |
| Melanoid pigmentation | − | − | − | − | ND |
| Morphology - cobweb | + | + | + | + | + |
| NaCl tolerance-% | 8 | 8 | 8 | 10 | ND |
| Nitrite from nitrate | − | − | − | + | − |
| Phosphatase | + | + | + | + | ND |
| Resistance to | | | | | |
| bacitracin | − | − | − | − | ND |
| lysozyme | + | + | + | + | − |
| novobiocin | − | − | − | + | ND |
| penicillin G | + | + | + | + | ND |

TABLE 4-continued

| Characteristic | A51568.1 | NRRL 2451 | NRRL 2452 | ATCC 19795 | N. orientalis |
|---|---|---|---|---|---|
| Comparison of Physiological Properties of A51568.1 and N. orientalis Reference Strains | | | | | |
| rifampin | + | + | + | + | + |
| Spore color | GY-W | W-Y | W-Y | W-Y | W-Y |
| Spore shape spherical to cylindrical | + | + | + | + | + |
| Spore surface, smooth | + | + | + | + | + |
| Survival at 50° C., 8h | + | + | + | + | + |
| Temperature range, °C. | 10-20 | 15-40 | 15-40 | 10-40 | 10-40 |
| Type A sugar pattern | + | + | + | + | + |
| Urease production | + | + | + | + | + |
| Utilization pattern of carbon compounds | + | + | + | + | + |
| Utilization pattern of organic acids | + | + | + | + | + |
| Vegetative growth optimum in the same medium | + | + | + | + | ND |

ND = not done

Further, the acid production from carbohydrates by cultures A51568.1, NRRL 2451, NRRL 2452, and ATCC 19795 was compared with the published results of 21 N. orientalis reference strains. This information is recorded in Table 5, which follows.

TABLE 5

Acid Production From Carbohydrates by Cultures A51568.1, NRRL 2451, NRRL 2452, ATCC 19795, and N. orientalis Reference Strains

| Characteristic | A51568.1 | NRRL 2451 | NRRL 2452 | ATCC 19795 | N. orientalis |
|---|---|---|---|---|---|
| Adonitol | − | + | + | + | + |
| l(+) Arabinose | + | + | + | + | + |
| Cellobiose | + | + | + | + | + |
| Cellulose | − | − | − | − | ND |
| Dulcitol | − | − | − | − | ND |
| i-Erythritol | + | + | + | + | + |
| Fructose | + | + | + | + | ND |
| d(+) Galactose | + | + | + | + | ND |
| Glucose | + | + | + | + | + |
| Glycerol | + | + | + | + | + |
| i-Inositol | + | + | + | + | + |
| Inulin | + | + | + | + | ND |
| d(+) Lactose | + | + | + | + | + |
| d(+) Maltose | + | + | + | + | + |
| d(−) Mannitol | + | + | + | + | + |
| d(+) Mannose | + | + | + | + | + |
| d(+) Melezitose | + | + | + | − | − |
| d(+) Melibiose | − | − | − | − | − |
| α-Me—D-Glucoside | + | + | + | + | + |
| d(+) Raffinose | − | − | − | − | − |
| l(+) Rhamnose | − | − | − | + | − |
| Salicin | + | + | + | + | ND |
| d(−) Sorbitol | − | − | − | − | − |
| Sucrose | + | + | + | + | ND |
| d(+) Trehalose | + | + | + | + | + |
| d(+) Xylose | + | + | + | + | + |
| Control | − | − | − | − | − |

ND = not done

Using the cultural, morphological, and physiological characteristics determined for A51568.1, comparison was made with the published descriptions of 14 taxa of Nocardia, as published by R. E. Gordon et al., "Some Bits and Pieces of the Genus Nocardia: N. carnea, N. vaccinii, N. transvalensis, N. orientalis, and N. aerocolonigenes", J. Gen. Microbiol. 109, 69-78 (1978); and by S. J. Mishra et al., "Identification of Nocardia and Streptomycetes of Medical Importance", J. Clin. Microbiol. 11(6), 728-736 (1980). In addition, simultaneous laboratory comparisons were made between culture A51568.1 and cultures NRRL 2451, NRRL 2452, and ATCC 19795.

Similarity coefficients were then calculated from the equation $$S = [Ns^+ + Ns^-]/[Ns^+ + Ns^- + Nd] \times 100$$

where $Ns+$ = *number of positive similarities*

$Ns-$ = number of negative similarities $Nd$ = number of dissimilarities (differences)

See: W. A. Kurylowicz et al., "Numerical Taxonomy of Streptomycetes", Polish Medical Publishers, Warsaw (1975).

The properties used to calculate similarity coefficients were mainly physiological characteristics. Comparisons were made by measuring all the other strains against culture A51568.1 Thus, A51568.1 compared to itself was rated as 100. The comparisons arre recorded in Table 6, which follows.

TABLE 6

Coefficient of Similarity Between Culture A51568.1 and Several Nocardia Reference Strains

| Culture | Coefficient |
|---|---|
| A51568.1 | 100 |
| NRRL 2451 | 95 |
| NRRL 2452 | 95 |
| ATCC 19795 | 86 |
| N. orientalis (composite of 21 strains) | 89 |
| N. aerocolonigenes | 76 |
| N. hirsuta | 68 |
| N. autotrophia | 65 |
| N. dassonvillei | 63 |
| N. madurea | 63 |
| N. brasiliensis | 61 |
| N. caviae | 61 |
| N. transvalensis | 57 |
| N. amarae | 53 |
| N. vaccinii | 50 |
| N. asteroides | 47 |
| N. carnea | 47 |
| N. pelletieri | 39 |

A comparison of the similarities and differences between culture A51568.1 and N. orientalis ATCC 19795 is set forth in Table 7, which follows.

TABLE 7

Similarities and Differences of Culture
A51568.1 and culture ATCC 19795

| Similarities | Differences |
|---|---|
| Acid from carbohydrates | Cultural characteristics on |
| Aerial hyphae | some media: |
| Catalase production | aerial mycelia color |
| Cell wall type IV | reverse color |
| Conidia present | soluble pigmentation |
| Cultural characteristics | Decomposition of xanthine |
| Decomposition of: | NaCl tolerance |
| casein | Nitrate reduction |
| DNA | Resistance to novobiocin |
| hypoxanthine | |
| tyrosine | |
| Fragmentation of mycelium | |
| Gelatin liquefaction | |
| Hydrolysis of: | |
| esculin | |
| hippurate | |
| skim milk | |
| starch | |
| Inability to decompose adenine | |
| Melanoid pigments absent | |
| Morphology | |
| Phosphatase production | |
| Resistance to: | |
| lysozyme | |
| penicillin | |
| rifampin | |
| Sensitivity to bacitracin | |
| Spore shape | |
| Spore surface ornamentation | |
| Staining reaction | |
| Sugar pattern of whole cell hydrolysates type A | |
| Survival at 50° C. for 8 hrs. | |
| Temperature range (10–40° C.) | |
| Urease production | |
| Utilization of organic compounds | |
| Vegetative growth in CSM medium | |

Culture A51568.1 has been deposited and made a part of the stock culture collection of the Northern Regional Research Center, U.S. Department of Agriculture, Agricultural Research Service, Peoria, Ill. 61604, from which it is available to the public under the number NRRL 15232.

Also a part of this invention are the pharmaceutically-acceptable, non-toxic salts of antibiotic A51568. "Pharmaceutically-acceptable" salts are salts in which the toxicity of the compound as a whole toward warm-blooded animals is not increased relative to the non-salt form. Representative and suitable salts of antibiotic A51568 include those acid addition salts formed by standard reaction with both organic and inorganic acids such as, for example, sulfuric, phosphoric, hydrochloric, acetic, succinic, citric, lactic, maleic, and fumaric; as well as those salts formed by the carboxyl group with strong bases such as sodium hydroxide, potassium hydroxide, sodium carbonate, potassium carbonate, ammonium hydroxide, diethanolamine, and like bases.

The activity of antibiotic A51568 against a variety of bacteria, as determined by the agar-dilution method, is reported in Table 8, which follows, wherein the minimum inhibitory concentration (MIC) values are recorded.

TABLE 8

ACTIVITY OF A51568 AGAINST
A VARIETY OF BACTERIA

| Bacteria | MIC (μg./ml.) |
|---|---|
| *Staphylococcus aureus* | |
| 3055* | 0.5 |
| X400 | 1 |
| V138 | 1 |
| V140 | 1 |
| V102 | 1 |
| *Staphylococcus epidermidis* | |
| 222 | 1 |
| 270 | 2 |
| 285 | 2 |
| 219 | 1 |
| 269 | 2 |
| *Streptococcus pyogenes* | |
| C203 | 0.5 |
| ATCC 10389 | 0.5 |
| *Streptococcus sp.* Group B | |
| 5 | 4 |
| 14 | 0.5 |
| *Streptococcus sp.* Group D | |
| X66 | 1 |
| 9960 | 4 |
| 2041 | 2 |
| 8043 | 1 |
| 9901 | 2 |
| 12253F | 1 |
| Mx161 | 1 |
| 2058 | 4 |
| *Streptococcus pneumoniae* | |
| Park I | 0.125 |
| Bl-438 | 0.5 |
| *Haemophilus parainfluenzae* | |
| 7901 | 64 |
| 9796 | 64 |
| *Haemophilus influenzae* | |
| C.L. | 32 |
| Mx366 | 32 |
| Mx371 | 64 |
| 76 | 64 |
| Bond | 64 |
| 16836 | 128 |
| 4842 | 32 |
| 312 | 128 |

*The name or number appearing under each organism identifies the strain of the organism empolyed in the test.

The in vitro activity of antibiotic A51568 against a number of aerobic bacteria has been determined using a standard agar-dilution assay. The results, determined by reading the end point after 24 hours, are recorded in Table 9, which follows.

TABLE 9

ACTIVITY OF A51568 AGAINST
AEROBIC BACTERIA

| Test Organism | MIC (μg./ml.) |
|---|---|
| *Staphylococcus aureus* 3055 | 1 |
| *Staphylococcus aureus* V41 | 1 |
| *Staphylococcus aureus* X400 | 2 |
| *Staphylococcus aureus* S13E | 1 |
| *Staphylococcus epidermidis* EPI1 | 2 |
| *Staphylococcus epidermidis* EPI2 | 1 |
| *Streptococcus pyogenes* C203 | 1 |
| *Streptococcus pneumoniae* Park I | 0.5 |
| Streptococcus sp. Group D X66 | 1 |
| Streptococcus sp. Group D 9960 | 4 |
| *Haemophilus influenzae* (sensitive) Holt | 64 |
| *Haemophilus influenzae* (resistant) R252 | 128 |
| *Escherichia coli* N10 | >128 |
| *Escherichia coli* EC14 | >128 |
| *Escherichia coli* TEM | 128 |
| *Klebsiella pneumoniae* X26 | >128 |
| *Klebsiella pneumoniae* KAE | >128 |

Antibiotic A51568 has been tested and found to be active against a number of anaerobic bacteria, as recorded in Table 10, which follows, the MIC values having been determined by the agar-dilution method.

TABLE 10

ACTIVITY OF A51568 AGAINST ANAEROBIC BACTERIA

| Test Organism | MIC (μg./ml.) |
| --- | --- |
| *Clostridium difficile* 2994 | 2 |
| *Clostridium perfringens* 81 | 1 |
| *Clostridium septicum* 1128 | 1 |
| *Eubacterium aerofaciens* 1235 | 2 |
| *Peptococcus asaccharolyticus* 1302 | 16 |
| *Peptococcus prevoti* 1281 | 32 |
| *Peptostreptococcus anaerobius* 1428 | 1 |
| *Peptostreptococcus intermedius* 1264 | 1 |
| *Propionibacterium acnes* 79 | 1 |
| *Bacteroides fragilis* 111 | 32 |
| *Bacteroides fragilis* 1877 | 32 |
| *Bacteroides fragilis* 1936B | 32 |
| *Bacteroides thetaiotaomicron* 1438 | 32 |
| *Bacteroides melaninogenicus* 1856/28 | >128 |
| *Bacteroides melaninogenicus* 2736 | 16 |
| *Bacteroides vulgatis* 1211 | 32 |
| *Bacteroides corrodens* 1874 | 32 |
| *Fusobacterium symbiosum* 1470 | 2 |
| *Fusobacterium necrophorum* 6054A | 2 |

Antibiotic A51568 is also active against a number of strains of *Clostridium difficile*, as determined by the agar-dilution method. The results of the tests are recorded in Table 11, which follows.

TABLE 11

ACTIVITY OF ANTIBIOTIC A51568 AGAINST *CLOSTRIDIUM DIFFICILE* STRAINS

| *Clostridium difficile* | MIC (μg./ml.) |
| --- | --- |
| 8484 | 2 |
| 6890 | 2 |
| 2634 | 2 |
| 78 | 2 |
| A-194 | 2 |
| A-195 | 2 |
| A-196 | 2 |
| A-279 | 2 |
| A-280 | 2 |
| A-281 | 2 |
| WAL-2112 | 2 |
| WAL-3657 | 2 |
| WAL-4268 | 2 |
| 107B | 2 |
| 111F | 2 |
| 1153 | 2 |
| 3424-5B | 2 |
| 3816 | 2 |
| 3950D | 2 |

Antibiotic A51568 has shown in vivo antimicrobial activity against experimental bacterial infections. When two doses of test compound were administered subcutaneously to mice in illustrative infections, the activity observed is measured as an $ED_{50}$ [effective dose in mg/kg to protect fifty percent of the test animals: See Warren Wick et al., *J. Bacteriol.* 81, 233–235 (1961)]. The $ED_{50}$ values observed for antibiotic A51568 are as follows:

| *Staph. aureus* 3055 | 1.79 mg/kg × 2 |
| --- | --- |
| *Strep. pyogenes* C203 | 3.03 mg/kg × 2 |
| *Strep. pneumoniae* Park I | 2.71 mg/kg × 2 |

In one of its aspects this invention provides a method for treating infections in man or animals which comprises administering to said man or animal a non-toxic antibiotic-effective dose of between about 25 mg. and about 2,000 mg. of antibiotic A51568, or a pharmaceutically-acceptable, non-toxic salt of the antibiotic.

In the treatment of infections in man, the antibiotic is administered by the parenteral route, e.g., by i.m. injection, or i.v. infusion. For injection, the antibiotic, or a pharmaceutically-acceptable diluent at the desired concentration and administered. Suitable diluents include, for example, Water-for-Injection, 0.9% saline, 5% dextrose, Ringer's solution, or other commonly employed diluent. For administration by i.v. infusion, the antibiotic or salt thereof can be made up in a physiological fluid or dilute nutrient at a suitable concentration; for example, at a concentration between about 5% and about 10%, and slowly infused with the fluid. Alternatively, the antibiotic may be administered by the "piggy-back" method.

The antibiotic, or the pharmaceutically-acceptable, non-toxic salts thereof can be made up in dosage unit formulations in hermetically sealed vials, sterile, rubber-stoppered vials, or in plastic pouches. Such unit dosage forms can contain excipients such as antioxidants, solubilizing agents, dispersing agents, buffers, and the like. One such dosage unit formulation comprises 100 mg. of A51568 antibiotic, or a pharmaceutically-acceptable, non-toxic salt thereof, in a rubber (butyl rubber) stoppered vial. Another dosage unit formulation comprises 250 mg. of antibiotic A51568, or a salt thereof, in a sterile, sealed vial. For i.v. infusion, a dosage unit formulation of this invention comprises 5 g. of antibiotic A51568, or a pharmaceutically-acceptable, non-toxic salt thereof, in a plastic pouch.

When antibiotic A51568 is used as an antibacterial agent, it may be administered either orally or parenterally. As will be appreciated by those skilled in the art, the A51568 antibiotic is commonly administered together with a pharmaceutically-acceptable carrier or diluent. The dosage of A51568 antibiotic will depend upon a variety of considerations, such as, for example, the nature and severity of the particular infection to be treated. Those skilled in the art will recognize that appropriate dosage ranges and/or dosage units for administration may be determined by considering the MIC and $ED_{50}$ values herein provided, together with factors such as the patient or host, and the infecting organism.

The A51568 antibiotic is useful inter alia for suppressing the growth of Staphylococcus, Streptococcus, and *Propionibacterium acnes* organisms, and the antibiotic could therefore be used, for example, in the treatment of acne. The A51568 antibiotic, in purified state, can be formulated in pharmaceutically-acceptable diluents such as isopropyl alcohol for application to the skin. Such solutions can be made up with antibiotic concentrations of from about 1 to about 15 percent weight per volume. Alternatively, the antibiotic can be made up into creams or lotions for application to the skin.

Antibiotic A51568 is also useful for suppressing the growth of *Clostridium difficile* organisms, which cause pseudomembranous colitis in the intestine. The A51568 antibiotic could therefore be used in the treatment of pseudomembranous colitis by the oral administration of an effective dose of the antibiotic or a pharmaceutically-acceptable, non-toxic salt thereof, prepared in a pharmaceutically-acceptable dosage form. For such use the A51568 antibiotic can be administered in gelatin capsules or in liquid suspension.

The antibiotic A51568 is produced by culturing the previously undescribed microorganism *Nocardia orientalis* NRRL 15232, or an A51568-producing mutant or varient thereof, in a culture medium containing assimilable sources of carbon, nitrogen, and inorganic salts, under submerged aerobic fermentation conditions until a substantial level of antibiotic activity is produced. Most of the antibiotic activity is found in the broth, while minor amounts of antibiotic activity may be associated with the mycelia. The A51568 antibiotic is most readily separated from the fermentation mixture by removal of the mycelia, i.e., the biomass, by filtration. The antibiotic is then isolated from the filtered fermentation broth, preferably by column chromatography over a suitable adsorbent using an appropriate eluting agent.

Suitable adsorbents include carbon, anion and cation exchange resins, polyamide, carboxymethylcelluloses, highly porous copolymers of styrene and divinylbenzene such as Diaion HP-20, the Amerlite XAD resins, and the Duolite resins such as hydrophilic, insoluble, molecular-sieve chromatographic mediums made by cross-linking dextran, and also TSK Gels. The Diaion resins are a product of Mitsubishi Chemical Industries, Limited, Tokyo, Japan. The Amberlite XAD resins are produced by Rohm and Haas, Philadelphia, Pa. The Duolite resins are products of Diamond Shamrock, Redwood City, Calif. Sephadex resins are manufactured by Pharmacia Fine Chemicals AB, Uppsala, Sweden. The TSK Gels are available from E. Merck, Darmstadt, Germany, and from Bio-Rad, 2200 Wright Ave., Richmond, Calif., 94804.

A number of different media may be used with *Nocardia orientalis* NRRL 15232, to produce the A51568 antibiotic. For economy in production, optimal yield, and ease of product isolation, however, certain culture media are preferred. These media should contain assimilable sources of carbon, nitrogen, and inorganic salts. Suitable carbon sources include potato dextrin, blackstrap molasses, glucose, sucrose, lactose, maltose, and starch. Optimum levels of carbon sources are from about 2 to about 5 percent by weight.

Preferred nitrogen sources include sodium glutamate, meat peptone, sodium nitrate, ammonium nitrate, ammonium sulfate, soybean grits, and yeast.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

It may be necessary to add small amounts (i.e., 0.2 ml/L) of an antifoam agent such as propyleneglycol to large-scale fermentation media if foaming becomes a problem.

Although small quantities of the A51568 antibiotic may be obtained by shake-flask culture, submerged aerobic fermentation in tanks is preferred for producing substantial quantities of the A51568 antibiotic. For tank fermentation, it is preferable to use a vegetative inoculum. The vegetative inoculum is prepared by inoculating a small volume of culture medium with the spore form, or mycelial fragments, to obtain a fresh, actively growing culture of the organism. The vegative inoculum is then transferred to a larger tank where, after a suitable incubation time, the A51568 antibiotic is produced in optimal yield.

An alternate method of providing inoculum for the vegetative medium consists of substituting a lyophilized pellet for the aqueous spore suspension. Lyophilized pellets are prepared in a manner known in the art. Preparation of the spore suspension for lyophilization is similar to the preparation of the aqueous spore suspension, except that sterile calf serum is substituted for sterile distilled water.

The A51568-producing organism can be grown over a broad temperature range of from about 25° to about 37° C. Optimum production of the A51568 antibiotic appears to occur at a temperature of about 30° C.

As is customary in aerobic submerged culture processes, sterile air is dispersed through the culture medium. For efficient growth of the organism, the volume of the air used in tank production is in the range of from about 0.1 to about 0.25 volumes of air per volume of culture medium per minute (v/v/m), with from about 100 to about 300 RPM agitation. An optimum rate in a 165-liter vessel containing 100 liters of fermentation medium is about 0.15 v/v/m, with agitation provided by an impeller rotating at about 200 RPM.

Antibiotic activity is generally present after about 24 hours and remains present for at least 168 hours during the fermentation period. Peak antibiotic production occurs at from about 90 hours to about 114 hours fermentation time.

The antibiotic activity is present in the supernatant. To sample, a whole broth sample is centrifuged for about 15 minutes at $1000 \times g$, and the centrate removed for assay. The assay is done microbiologically by an agar well plate test employing *Micrococcus luteus* ATCC 9341.

Production of the A51568 antibiotic can be monitored during the fermentation by either agar diffusion using *Bacillus subtilis* ATCC 6633, or a turbidimetric method using *Staphylococcus aureus* ATCC 9114.

In order to illustrate more fully the operation of this invention, the following Examples are provided.

EXAMPLE 1

Preparation of First Stage Inoculum

The following medium was prepared for use in the agar slant culture of *Nocardia orientalis* NRRL 15232:

| Ingredient | Amount (g/L) |
| --- | --- |
| Precooked oatmeal | 60.0 |
| Yeast | 2.5 |
| $K_2HPO_4$ | 1.0 |
| Czapek's mineral stock | 5.0 ml/L |
| Agar | 25.0 |
| Deionized water | q.s. to 1.0 liter |

Czapek's mineral stock is prepared from the following ingredients:

| Ingredient | Amount (g/100 ml) |
| --- | --- |
| KCl | 10.0 |
| $MgSO_4.7H_2O$ | 10.0 |
| $FeSO_4.7H_2O$ | 0.2 |
| Deionized water | q.s. to 100 ml. |

Pre-sterilization pH=6.2 Adjusted to pH 7.3 with aqueous sodium hydroxide solution. Post-sterilization pH=6.7.

Spores of *Nocardia orientalis* NRRL 15232 were inoculated on an agar slant made up of the above-identified ingredients, and the thus-inoculated slant was incubated for seven days at about 30° C. The mature slant culture was then covered with sterile distilled water and scraped with a sterile tool to loosen the spores and the mycelium. One milliliter of the resulting spore suspension was used to inoculate 50 ml of vegetative medium having the following composition:

| Ingredient | Amount (g/L) |
| --- | --- |
| Potato dextrin | 30.0 |
| Molasses, blackstrap | 20.0 |
| Bacto-peptone (Difco Laboratories) | 7.0 |
| L-Tyrosine | 1.0 |
| Deionized water | q.s. to 1.0 liter |

The mixture had pH=5.5, which was adjusted to pH 7.0 with aqueous sodium hydroxide solution before sterilization. Post-sterilization pH=6.1.

The vegetative inoculum was incubated in a 250-ml wide-mouth Erlenmeyer flask at about 30° C. for about 48 hours on a shaker rotating through an arc two inches in diameter at 250 RPM. This incubated medium is used either to inoculate small fermenters (the inoculum being 0.8% per volume of medium) or to inoculate second stage flasks for the production of a larger volume of mycelium.

Fermentation of A51568.1

One hundred liters of a production medium was inoculated with 0.8% (800 ml) of the incubated vegetative medium from above. The production medium had the following composition:

| Ingredient | Amount (g/L) |
| --- | --- |
| Polypropyleneglycol (2000) | 0.2 |
| Potato dextrin | 30.0 |
| Blackstrap molasses | 20.0 |
| Bacto-peptone (Difco Laboratories) | 7.0 |
| L-Tyrosine | 1.0 |
| Deionized water | q.s. to 100 liters |

The medium had pH 5.2, which was adjusted to 7.1 with aqueous 5N sodium hydroxide. The medium was sterilized at 121° C. at 17–19 psi. for 45 minutes. After sterilization, the medium had pH 6.2.

The inoculated production medium was allowed to ferment in a 165-liter fermentation tank for about 114 hours at a temperature of 30° C. The fermentation medium was aerated with sterile air at a rate of 0.15 v/v/m, and was stirred with conventional agitators at about 200 RPM.

The antibiotic activity is present in the supernatant of the fermentation mixture. The presence of the antibiotic activity was checked by centrifuging a sample of the whole broth at 1000×g, and decanting the centrate for assay. The sample is diluted with pH 6.0 phosphate buffer, and assayed microbiologically in an agar-well plate test using as assay organism *Micrococcus luteus* ATCC 9341.

The fermentation was also monitored qualitatively by a thin-layer chromatography (TLC) system using silica gel #5763 or #5765 plates from E. Merck, Darmstadt. The plates were developed in a solvent system containing chloroform:methanol:ammonia:n-butanol:water (25:50:25:10). The chromatograms were bioautographed versus *Bacillus subtilis* ATCC 6633 on nutrient agar plates.

Employing the chloroform:methanol:ammonia:n-butanol:water (25:50:25:10) solvent, the antibiotic A51568 has been determined to have an $R_f$ value of 0.6.

EXAMPLE 2

Isolation of Antibiotic A51568

To three liters of antibiotic A51568 whole fermentation broth there was added filter aid (Hyflo Supercel, a diatomaceous earth, Johns-Manville Corp.), and the mixture filtered. The filtrate, which measured 2.7 liters and had pH=7.8, was applied to Diaion HP-20 resin (a highly porous, styrenedivinylbenzene copolymer in bead form, Mitsubishi Chemical Industries, Ltd., Tokyo, Japan) contained in a 3×25 cm chromatography column. The effluent was discarded, and the column washed with 1 liter of water and 500 ml of 25 percent methanol in water. The antibiotic A51568 was eluted from the column with two 500-ml portions of 50 percent methanol in water. The eluant was assayed for antibiotic activity using *B. subtilis*. The more active fraction was concentrated to a small volume and lyophilized. Crude antibiotic A51568 weighing 905 mg was obtained.

EXAMPLE 3

Purification of Antibiotic A51568

The crude antibiotic A51568 (905 mg, from Example 2, above) was dissolved in 50 ml of water and applied to Sephadex CM-25 (NH$_4$+cycle) (Pharmacia Fine Chemicals AB, Uppsala, Sweden) contained in a 1.7×44 cm chromatography column. The effluent was discarded and the column washed with 250 ml of water. The column was then eluted with a convex gradient of ammonium bicarbonate (H$_2$O→1M NH$_4$HCO$_3$; 100 ml mixing chamber). Fifty 25-ml fractions were collected and checked for antibiotic activity using a *B. subtilis* assay.

Active fractions, that is, those containing antibiotic activity, were pooled and applied to a 1.7×10 cm chromatography column of Diaion HP-20 resin previously equilibrated in water. After the application of the antibiotic solution, the column was washed with 200 ml of water and eluted with 100 ml of 50 percent methanol in water. The methanol eluate was evaporated to dryness, the residue dissolved in a small amount of water and acidified with 0.1N aqueous hydrochloric acid. The acidified mixture was then lyophilized. There was obtained 25 mg of pure antibiotic A51568.

We claim:

1. Antibiotic A51568, which has the structure and its pharmaceutically-acceptable, non-toxic salts.

2. The method for treating bacterial infections in a mammal which comprises administering to the mammal a therapeutically-effective dose of the antibiotic compound of claim 1, or a pharmaceutically-acceptable, non-toxic salt thereof.

3. A pharmaceutical composition suitable for the treatment of bacterial infections in a mammal which comprises as the active ingredient the antibiotic compound of claim 1, or a pharmaceutically-acceptable, non-toxic salt thereof, and a pharmaceutically-acceptable carrier.

* * * * *